United States Patent
Krichtafovitch et al.

(10) Patent No.: US 12,121,911 B1
(45) Date of Patent: Oct. 22, 2024

(54) SUPERVISORY CONTROL AND PATHOGEN-DESTROYING ELECTROSTATIC PRECIPITATOR SYSTEM

(71) Applicant: AGENTIS AIR LLC, Columbia, MD (US)

(72) Inventors: Igor Krichtafovitch, Kiev (UA); Alan Viosca, Seattle, WA (US); Larry Rothenberg, Kensington, MD (US)

(73) Assignee: AGENTS AIR LLC, Columbia, MD (US)

( * ) Notice: Subject to any disclaimer, the term of this patent is extended or adjusted under 35 U.S.C. 154(b) by 0 days.

(21) Appl. No.: 18/208,842

(22) Filed: Jun. 12, 2023

Related U.S. Application Data

(63) Continuation-in-part of application No. 18/208,844, filed on Jun. 12, 2023, and a continuation-in-part of application No. 18/208,847, filed on Jun. 12, 2023, and a continuation-in-part of application No. 18/208,845, filed on Jun. 12, 2023.

(Continued)

(51) Int. Cl.
| | |
|---|---|
| *B03C 3/68* | (2006.01) |
| *A61L 9/015* | (2006.01) |
| *A61L 9/16* | (2006.01) |
| *B01D 53/32* | (2006.01) |
| *B01D 53/86* | (2006.01) |
| *B03C 3/017* | (2006.01) |
| *B03C 3/36* | (2006.01) |

(52) U.S. Cl.
CPC ............... *B03C 3/68* (2013.01); *A61L 9/015* (2013.01); *A61L 9/16* (2013.01); *B01D 53/323* (2013.01); *B01D 53/8675* (2013.01); *B03C 3/017* (2013.01); *B03C 3/36* (2013.01); *A61L 2209/111* (2013.01); *A61L 2209/134* (2013.01); *A61L 2209/14* (2013.01); *A61L 2209/16* (2013.01); *B01D 2257/106* (2013.01); *B01D 2257/91* (2013.01); *B01D 2259/818* (2013.01)

(58) Field of Classification Search
CPC .. B03C 3/68; B03C 3/017; B03C 3/36; A61L 9/015; A61L 9/16; A61L 2209/111; A61L 2209/134; A61L 2209/14; A61L 2209/16; B01D 53/323; B01D 53/8675; B01D 2257/106; B01D 2257/91; B01D 2259/818
USPC ....................................................... 422/105
See application file for complete search history.

(56) References Cited

U.S. PATENT DOCUMENTS

| | | | |
|---|---|---|---|
| 895,729 A | 8/1908 | Cottrell | |
| 3,915,672 A * | 10/1975 | Penney | ..................... B03C 3/38 96/25 |

(Continued)

OTHER PUBLICATIONS

U.S. Appl. No. 63/351,339, filed Jun. 12, 2022, Igor Krichtafovitch, Entire Document.

(Continued)

*Primary Examiner* — Huy Tram Nguyen
(74) *Attorney, Agent, or Firm* — Ungerman IP PLLC; Mark E. Ungerman

(57) ABSTRACT

An electrostatic air cleaner may be operated according to a manner designed to achieve acceptable air quality while balancing power usage and corona electrode degradation levels. The voltage applied to the corona electrode(s) may be controlled as well as the voltage applied to repelling electrodes and air flow velocity. The air cleaner may also be operated to achieve desired particle separation.

13 Claims, 6 Drawing Sheets

Related U.S. Application Data

(60) Provisional application No. 63/351,411, filed on Jun. 12, 2022, provisional application No. 63/351,339, filed on Jun. 10, 2022.

(56) References Cited

U.S. PATENT DOCUMENTS

| | | | |
|---|---|---|---|
| 6,504,308 | B1 | 1/2003 | Krichtafovitch et al. |
| 6,664,741 | B1 | 12/2003 | Krichtafovitch |
| 6,937,455 | B2 | 8/2005 | Krichtafovitch et al. |
| 7,594,958 | B2 | 9/2009 | Krichtafovitch et al. |
| 9,488,382 | B2 | 11/2016 | Krichtafovitch |
| 9,682,384 | B2 | 6/2017 | Afanasiev et al. |
| 9,808,808 | B2 | 11/2017 | Wen et al. |
| 9,827,573 | B2 | 11/2017 | Afanasiev et al. |
| 10,668,483 | B2 | 6/2020 | Krichtafovitch |
| 10,792,673 | B2 | 10/2020 | Krichtafovitch |
| 10,828,646 | B2 | 11/2020 | Rothenberg |
| 10,875,034 | B2 | 12/2020 | Krichtafovitch |
| 10,882,053 | B2 | 1/2021 | Krichtafovitch |
| 10,960,407 | B2 | 3/2021 | Krichtafovitch |
| 11,123,750 | B2 | 9/2021 | Krichtafovitch |
| 2017/0354977 | A1 | 12/2017 | Krichtafovitch |
| 2018/0001548 | A1 | 1/2018 | Dietrich et al. |
| 2020/0360936 | A1* | 11/2020 | Lee .................... B01D 46/681 |
| 2020/0368384 | A1* | 11/2020 | Rosenørn ........... B01D 53/8675 |

OTHER PUBLICATIONS

U.S. Appl. No. 63/351,411, filed Jun. 12, 2022, Igor Krichtafovitch, Entire Document.

Conductive Polymer, Wikipedia, pp. 10, retrieved from https://en.wikipedia.org on Jun. 7, 2022.

EPA, Guide to Air Cleaners in the Home, 2nd Edition, Portable Air Cleaners Furnace and HVAC Filters, Jul. 2018, pp. 7, US, retrieved from www.epa.gov.

EPA, Residential Air Cleaners, A Technical Summary, 3rd Edition, Portable Air Cleaners Furnace and HVAC Filers, Jul. 2018, pp. 74, US, retrieved from www.epa.gov.

Jane H. Davidson & Peter J. McKinney, Chemical Vapor Deposition in the Corona Discharge of Electrostatic Air Cleaners, Aerosol Science and Technology, Aug. 1998, vol. 29:2, Taylor & Francis Group, retrieved https://www.tandfonline.com.

Lew Harriman, et al., New Guidance for Residential Air Cleaners, ASHRAE Journal, Sep. 2019, pp. 8, retrieved from URL www.ashrae.org.

M.B. Awad & GSP Castle, Ozone Generation in an Electrostatic Precipitator With a Heated Corona Wire, Journal of the Air Pollution Control Association, Apr. 1975, vol. 25, No. 4, Taylor & Francis Group, retrieved from https://www.tandfonline.com.

RTP Imagineering Plastics, Conductive Thermoplastics, Reliable and Safe Solutions Using Thermoplastic Technologies, pp. 16, retrieved from www.rtpcompany.com.

* cited by examiner

SUPERVISORY CONTROL AND PATHOGEN-DESTROYING ELECTROSTATIC PRECIPITATOR SYSTEM

CROSS REFERENCE TO RELATED APPLICATIONS

This present application claims priority to provisional Application No. 63/350,866 filed Jun. 9, 2022, the disclosure of which is expressly incorporated herein. This application also claims priority to and has subject matter related to non-provisional application Ser. No. 18/208,844 and non-provisional application Ser. No. 18/208,847, both filed on even date herewith and having the same applicant as this application. This application claims priority to provisional Application No. 63/351,339 filed Jun. 10, 2022 and provisional application 63/351,411. The subject matter of this application relates to non-provisional Application Ser. No. 18/208,845 filed on the same date and having the same applicant as this application and which claims priority to provisional Application No. 63/351,411 filed Jun. 12, 2022). The disclosures of all of the applications mentioned above are expressly incorporated by reference herein.

BACKGROUND OF THE INVENTION

1. Field of the Invention

The invention relates to electrostatic precipitators and more particularly to controls for electrostatic precipitators.

2. Description of the Related Technology

Indoor air quality (IAQ) is the air quality within and around buildings and structures. IAQ is known to affect the health, comfort, and well-being of building occupants. Poor indoor air quality has been linked to sick building syndrome, reduced productivity, and impaired learning in schools. Poor indoor air quality can increase risks to the health of its occupants and can increase pathogen levels and increase mortality rates. It is also confirmed that poor IAQ increases morbidity and mortality rate during pandemics like Covid-19.

IAQ can be affected by gases (including carbon monoxide, radon, and volatile organic compounds), particulates, microbial contaminants (mold, bacteria, viruses), or any mass stressor that can induce adverse health conditions. Source control, air filtration, and the use of ventilation to dilute contaminants are the primary methods for improving indoor air quality in most buildings. Residential units can further improve indoor air quality by routine cleaning of carpets and area rugs.

Determination of IAQ involves the collection of air samples, monitoring of human exposure to pollutants, collection of samples on building surfaces, and computer modeling of airflow inside buildings.

IAQ is part of indoor environmental quality (IEQ), which includes IAQ as well as other physical and psychological aspects of life indoors (e.g., lighting, visual quality, acoustics, radiation, and thermal comfort).

Indoor air pollution is a major health hazard. A major source of indoor air pollution is the burning of biomass for heating and cooking. This results in high concentrations of particulate matter.

Indoor workplaces are found in many working environments such as offices, sales areas, hospitals, libraries, schools, and preschool childcare facilities. At such workplaces, no tasks involving hazardous substances are performed, and they do not include high-noise areas. Nevertheless, employees may exhibit symptoms belonging to the sick building syndrome such as the burning of the eyes, scratchy throat, blocked nose, and headaches.

There are many bacteria and viruses of health significance that may be and frequently are found in indoor air and on indoor surfaces.

Many common building materials used before 1975 contain asbestos, such as some floor tiles, ceiling tiles, shingles, fireproofing, heating systems, pipe wraps, taping muds, mastics, and other insulation materials. Normally, significant releases of asbestos fiber do not occur unless the building materials are disturbed, such as by vibrating the materials or walls including cutting, sanding, drilling, earthquakes, or building remodeling. Removal of asbestos-containing materials is not always optimal because the fibers can be spread into the air during the removal process. A management program for intact asbestos-containing materials is often recommended instead. When asbestos-containing material is damaged or disintegrates, microscopic fibers are dispersed into the air. Inhalation of asbestos fibers over long exposure times is associated with an increased incidence of lung cancer, in particular the specific form of mesothelioma. The risk of lung cancer from inhaling asbestos fibers is significantly greater for smokers, however, there is no confirmed connection to damage caused by asbestosis. The symptoms of the disease do not usually appear until about 20 to 30 years after the first asbestos exposure.

Asbestos is found in older homes and buildings but occurs most commonly in schools, hospitals, and industrial settings. Although all asbestos are hazardous, friable products, e.g., sprayed coatings and insulation, pose a significantly higher hazard as they are more likely to release fibers into the air. The US Federal Government and some states have set standards for acceptable levels of asbestos fibers in indoor air. There are particularly stringent regulations applicable to schools.

Atmospheric particulate matter, also known as particulates, can be found indoors and can affect the health of occupants. Authorities have established standards for the maximum concentration of particulates to ensure indoor air quality.

In 2015, experimental studies reported the detection of significant episodic (situational) cognitive impairment from impurities in the air breathed by test subjects who were not informed about changes in the air quality. Researchers at Harvard University and SUNY Upstate Medical University and Syracuse University measured the cognitive performance of 24 participants in three different controlled laboratory atmospheres that simulated those found in "conventional" and "green" buildings, as well as green buildings with enhanced ventilation. Performance was objectively evaluated using Strategic Management Simulation software simulation tool, a well-validated assessment test for executive decision-making in an unconstrained situation that permits initiative and improvisation. Significant deficits were observed in the performance scores achieved in increasing concentrations of either Volatile Organic Compounds ("VOCs") or carbon dioxide while keeping other factors constant. The highest impurity levels reached are not uncommon in some classroom or office environments.

The use of air filters can trap some air pollutants. The Department of Energy's Energy Efficiency and Renewable Energy section suggests that "[Air] Filtration should have a Minimum Efficiency Reporting Value (MERV) of 13 as determined by ASHRAE 52.2-1999." Cooling systems may include cooling coils that tend to gather condensate and may be wet. Those systems are known as sources of *Aspergillus niger*.

Air filters may be used to reduce the amount of dust that reaches the wet coils. Such dust is undesirable. When the dust contacts wet coils, the dust can serve as fertile soil to grow molds on the wet coils and in the ventilation ducts and can reduce the efficiency of the cooling. One of the biggest problems in electrostatic filters is an unwanted occasional electrical discharge between the electrodes. ASHRAE standard 52.2 stipulates air purifier testing using carbon black, which contains electrically conductive dust. In some industrial areas, most notoriously in China, so-called "Asian dust" also carries dust that contains electrically conductive particles. After a certain time of exposure to such dust, a conductive layer forms on the inter-electrode surfaces. The conductive layer may cause an electrical short between the electrodes.

Traditional media filters and HEPA filters (also known as mechanical filters) have the drawback of energy inefficiency and decreasing efficiency over time due to the clogging of filters. In high-pollution environments, the use of filters may require more energy for air movement. In addition, the use of media filters in high-pollution environments may result in a need for frequent replacement of the media filters. Mechanical filters are expensive and better filtration always comes at a substantial increase in cost due to energy and media costs. Another drawback to mechanical filters is the noise attributed to air movement devices like fans. The back pressure created by blocking mechanical filters must be overcome by fans, which can be noisy and annoying, particularly in residential settings. The backpressure at a mechanical media filter increases over time as the mechanical filter is loaded thereby requiring more force to push air past or through the mechanical filters. More force comes at the expense of greater noise and energy consumption.

Additional information is available from the US Environmental Protection Agency (EPA) and the American Society of Heating, Refrigerating and Air-Conditioning Engineers (ASHRAE). According to the EPA, the most effective ways to improve indoor air are to reduce or remove the sources of pollutants and to ventilate with clean outdoor air. In addition, research shows that filtration can be an effective supplement to source control and ventilation. Using a portable air cleaner and/or upgrading the air filter in your furnace or central heating, ventilation, and air-conditioning (HVAC) system can help to improve indoor air quality. Portable air cleaners, also known as air purifiers or air sanitizers, are designed to filter the air in a single room or area. A central furnace or HVAC filter is designed to filter the air throughout a home. Portable air cleaners and HVAC filters can reduce indoor air pollution; however, they cannot remove all pollutants from the air.

The following publications provide information on portable air cleaners and HVAC and furnace filters commonly used in homes.

The EPA has issued a short consumer guide covering portable air cleaners and furnace or HVAC filters used in a home. It includes tips for selecting a portable air cleaner, furnace filter, or HVAC filter. *Guide to Air Cleaners in the Home, 2nd edition, August* 2018 *Portable Air Cleaners, Furnace and HVAC Filters*, available online at: https://www.epa.gov/sites/production/files/2018-07/documents/guide_to_air_cleaners_in_the_home_2nd_edition.pdf the disclosure of which is expressly incorporated by reference herein.

The EPA has also issued guidance in the form of a technical summary *Residential Air Cleaners: A Technical Summary, 3rd edition, August* 2018 *Portable Air Cleaners Furnace and HVAC Filters*, available online at: https://www.epa.gov/sites/production/files/2018-7/documents/residential_air_cleaners_a_technical_summary_3rd_edition.pdf the disclosure of which is expressly incorporated by reference herein, focusing on air cleaners for residential use; it does not address air cleaners used in large or commercial structures such as office buildings, schools, large apartment buildings, or public buildings. In addition to providing general information about the types of pollutants affected by air cleaners, this document discusses the types of air-cleaning devices and technologies available, metrics that can be used to compare air-cleaning devices, the effectiveness of air-cleaning devices in removing indoor air pollutants, and information from intervention studies on the effects that air cleaners can have on health and health markers.

See also, Harriman, Stephens, Brennan—*New Guidance for Residential Air Cleaners—ASHRAE Journal September* 2019 (pdf) (September 2019), the disclosure of which is expressly incorporated by reference herein published by the American Society of Heating, Refrigerating, and Air-Conditioning Engineers (ASHRAE) See also the NAFA Guide to Air Filtration, $6^{th}$ edition, 2021, available here:
https://netforum.avectra.com/eweb/shopping/
shopping.aspx?site=nafa&webcode=shopping&prd
key=67ba3254-31ec-43ca-9ed8-67f0e8849a83.

An electrostatic precipitator (ESP) is a filtration device that removes fine particles, like dust and smoke, from a flowing gas using the force of an induced electrostatic charge minimally impeding the flow of gases through the unit.

Traditional ESPs apply energy only to the particulate matter being collected and therefore are very efficient in their consumption of energy (in the form of electricity). Electrostatic precipitators use corona discharge to generate ions. Early use of corona discharge to remove particles from an aerosol was proposed by Hohlfeld in 1824. However, electrostatic precipitators were not commercialized until almost a century later. In 1907 Frederick Gardner Cottrell, a professor of chemistry at the University of California, Berkeley, patented a device for charging particles and then collecting them through electrostatic attraction—the first electrostatic precipitator. See U.S. Pat. No. 895,729. Cottrell first applied the device to the collection of sulfuric acid mist and lead oxide fumes emitted from various acid-making and smelting activities.

At the time of Cottrell's invention, the theoretical basis for the operation was not understood. The operational theory was developed later in Germany, with the work of Walter Deutsch and the formation of the Lurgi company.

Electrophoresis is the term used for the migration of gas-suspended charged particles in a direct-current electrostatic field. The most basic precipitator contains a row of thin vertical wires, followed by a stack of large flat metal plates oriented vertically, with the plates typically spaced about 1 cm to 18 cm apart, depending on the application. The airstream flows horizontally through the spaces between the wires and then passes through the stack of plates.

A negative voltage of several thousand volts or tens of thousands of volts is applied between the wire and the plate. If the applied voltage is high enough, an electric corona discharge emits ions into the air around the electrodes, which then charges the particles in the air stream.

The charged particles, due to the electrostatic force, are diverted towards the collection (grounded) plates. Particles build up on the collection plates and are removed from the air stream.

Metal plate precipitators are commonly marketed to the public as air purifier devices or as a permanent replacement for furnace filters, but all have the undesirable attribute of being somewhat messy to clean. A negative side-effect of electrostatic precipitation devices is the potential production of toxic ozone and NO. However, electrostatic precipitators offer benefits over other air purification technologies, such as HEPA filtration, which require expensive filters and can become "production sinks" for many harmful forms of bacteria.

With electrostatic precipitators, if the collection plates are allowed to accumulate large amounts of particulate matter, the particles can sometimes bond so tightly to the metal plates that vigorous washing and scrubbing may be required to completely clean the collection plates. The close spacing of the plates can make thorough cleaning difficult, and the stack of plates often cannot be easily disassembled for cleaning. One solution, suggested by several manufacturers, is to wash the collector plates in a dishwasher.

Some consumer precipitation filters are sold with special soak-off cleaners, where the entire plate array is removed from the precipitator and soaked in a large container overnight, to help loosen the tightly bonded particulates.

A study by the Canada Mortgage and Housing Corporation testing a variety of forced-air furnace filters found that ESP filters provided the best, and most cost-effective means of cleaning the air using a forced-air system but were still subject to inconvenient plate cleaning requirements.

The Applicant has developed an ESP that uses a conductive layer sandwiched between non-conductive open cell material layers, as shown in U.S. Pat. Nos. 9,488,382 and 10,668,483 the disclosures of which are expressly incorporated by reference herein. Other patents assigned or licensed to Applicant include U.S. Pat. Nos. 9,682,384; 9,808,808; 9,827,573; 10,792,673; 10,828,646; 10,875,034; 10,882,053; 10,960,407; and 11,123,750. The disclosures of each of the identified patents are expressly incorporated by reference herein.

A known byproduct of corona discharge is the production of ozone. Because of the strongly oxidizing properties of ozone, ozone is a primary irritant, affecting especially the eyes and respiratory systems, and can be hazardous at even low concentrations.

To protect workers potentially exposed to ozone, U.S. Occupational Safety and Health Administration has established a permissible exposure limit (PEL) of 0.1 μmol/mol (29 CFR 1910.1000 table Z-1), calculated as an 8-hour time-weighted average. Higher concentrations are especially hazardous, and NIOSH has established an Immediately Dangerous to Life and Health Limit (IDLH) of 5 μmol/mol. Work environments where ozone is used or where it is likely to be produced should have adequate ventilation and it is prudent to have a monitor for ozone that will alarm if the concentration exceeds the OSHA PEL. The State of California has adopted air cleaner regulations to limit the amount of ozone produced by indoor air cleaning devices, to protect public health. The regulations require all air cleaner models marketed or sold in California after Oct. 18, 2010, to be tested and certified under the regulation. This included air cleaners sold via the Internet. ESPs may include ozone filters to absorb the ozone produced during corona discharge.

According to M. B. Awad, et al., Ozone Generation in an Electrostatic Precipitator With a Heated Corona Wire, *Journal of the Air Pollution Control Association*, 24 (4): 369 (April 1975), G.S.P. Castle, et al., "Ozone generation in positive corona electrostatic precipitators," *I.E.E.E. Trans.*, IGA-5 (4): 489 (1969), the disclosures of which are expressly incorporated by reference herein, two-stage electrostatic precipitators are widely used for high-efficiency collection of submicron particulates in air cleaning applications where recirculation of the air is required. In existing two-stage precipitators, a short positive corona section charges dust particles. The collection takes place in a downstream static electric field region. For best operation, it is important to ensure that the dust particles are charged to the maximum possible level and that the collection field strength is kept as high as possible. The upper level for the collection field strength is set by the electric breakdown strength of air. The precipitator is designed to produce the strongest possible field, short of breakdown, with a certain loading of dust on the collection plates.

The magnitude of the charge that is transferred to the particles is dependent on the corona current density that exists in the charging section. However, increasing the corona current also increases the amount of ozone that is generated by the discharge. Present American industrial standards limit the allowable exposure to $O_3$ to 0.10 ppm by volume for an 8-hour day. Therefore, to maintain acceptable $O_3$ concentrations for given air flows through the precipitator, it is necessary to keep the magnitude of the corona voltage below the spark threshold level. The spark threshold voltage level is the voltage at which spark-over occurs. The limiting design parameters required to minimize $O_3$ generation involve selecting a corona wire of the smallest possible diameter compatible with mechanical strength. A reduction in the $O_3$ levels may be obtained by heating the corona wire.

U.S. Pat. No. 7,594,958, the disclosure of which is expressly incorporated by reference herein, shows a spark management device that includes a high-voltage power source and a detector configured to monitor a parameter of an electric current provided to a load device. In response to the parameter, a pre-spark condition is identified. A switching circuit is responsive to the identification of the pre-spark condition for controlling the electric voltage provided to the load device to manage sparking. Management of sparking includes, but is not limited to, reducing the occurrence of sparks, eliminating sparks, regulating sparks, timing sparks, and/or controlling the intensity of any sparks generated.

In conventional electrostatic air purifiers, all the electrodes with different electrical potentials are attached to the common case walls and are separated by a certain distance along the surface of the walls. Once conductive dust is collected on the wall it may cause an electrical short between the electrodes. Such a short may be called a "creeping" discharge along the surface of the wall. US 2018/001548 A1, the disclosure of which is expressly incorporated herein by reference, shows an electrostatic air cleaner designed to reduce "creeping" discharge by extending the effective creeping distance by configuring the electrodes with opposing polarity to be mounted at locations spaced apart from each other.

U.S. Pat. No. 9,488,382, the disclosure of which is expressly incorporated herein by reference, entitled "Electronic Air Cleaners and Associated Systems and Methods" shows an electrostatic air cleaner that collects and removes particles such as dust, pollen, smoke, pathogens, and other contaminants from the air by use of electric corona discharge. The air cleaner has an ionizing stage and a collection stage. The ionizing stage has exciting electrodes and corona electrodes. The collection stage has collecting electrodes and repelling electrodes. The collecting electrodes have a conductive core between open-cell sheets. The open-cell sheets have a much greater surface area than a flat metal plate.

When a corona electrode is operated in an environment that includes certain chemicals, such as silicone, the chemical particles, which reduce performance, may accumulate on the electrodes. Accumulation of such chemical particles may require that the electrodes be cleaned or replaced from time to time. J. H. Davidson, P. J. Mckinney, *Chemical Vapor Deposition in the Corona Discharge of Electrostatic Air Cleaners*, Journal of Electrostatics, 29 (2): 102-110, 1998, expressly incorporated herein by reference.

US 2017/0354977 A1 shows an air cleaner and/or particle separator with electrodes of the same type kept at the same potential. The exciting electrode is one or more than one piece electrically connected. The corona electrodes may be a corona wire routed across the airflow path one time or more than one time and an electrostatic device may have one corona wire or multiple corona wires routed across an airflow path and electrically connected. The term "electrode set" is intended to include one or more electrodes of the same type. The corona electrode voltage as well as the collecting electrode voltage may be increased or decreased depending on the air volume of the air blower, collection efficiency, treatment amount, and level of air contamination to be treated. US 2017/0354977 A1, the disclosure of which is expressly incorporated herein by reference, describes an objective of having a low ozone generation at the corona discharge by reduction of the corona voltage. The air cleaner is provided with at least one air quality sensor positioned to monitor precipitator outlet air quality. A control system may be connected to the sensors and a power source. The control system may be connected to adjust the voltage at a power source output to at least two electrode sets. The control system may be responsive to the sensor to achieve an air quality goal at improved energy expenditure.

SUMMARY OF THE INVENTION

Contrary to the teachings of the prior art, the present design is of an electrostatic precipitator capable of enhancing ozone output or by undertaking other steps for pathogen destruction, for example increasing ion generation or density. It is an object to enhance the ozone output of an electrostatic precipitator and utilize the enhanced ozone output to destroy dangerous pathogens without exposing occupants to unsafe levels of ozone.

Electrostatic air cleaners may include an ion generator and a particle collector. The ion generator and particle collector may be housed with a fan, as a standalone appliance. The ion generator and particle collector may be in a constrained airflow path such as a ventilation duct or chimney/stack. In this case, the airflow is otherwise generated, such as by an HVAC system.

It is an object to provide an electrostatic air cleaner with the ability to be operated in an enhanced pathogen-killing mode. This enhanced pathogen-killing mode may be enabled by the air cleaner's ability to independently control power to the corona electrode assembly and airspeed around the ionizing assembly. In a pathogen-killing mode, these two functions may be operated by a control system to increase the concentration of ozone in and around the particle collection components of an electrostatic air cleaner. And increase in ozone concentration may simultaneously increase ion generation which may enhance pathogen destruction. In this manner, pathogens in and around the corona electrode assembly and the particle collection components of the electrostatic air cleaner may be destroyed. This may be used to decrease the pathogens on the particle collection components before being handled by a person, for example before collector assemblies are replaced, cleaned, or repaired. In addition, the destruction of pathogens on a particle collector will prevent live pathogens from being re-entrained in airflow and causing harm to the occupants of the building. In pathogen-killing mode, the power to the corona assembly may be increased, above the normal filtration mode operating power level, to increase the production of ozone. At the same time, the airflow through the air cleaner may be curtailed. Airflow may be curtailed by various mechanisms including decreased fan speed, shut-off fan, block airflow path, reverse airflow direction, or activating ionic wind effects. Airflow direction reversal may be accomplished by reversing the fan direction or by manipulating appropriately configured baffles. This results in enhancing ozone concentration around the collection electrodes.

A further object is to facilitate an increased ozone concentration in a particle collection assembly without exposing occupants to elevated ozone levels. This may be accomplished by interrupting the airflow through the electrostatic air cleaner. Interruption of airflow may be accomplished by reversing or simply turning off the fan or other air mover that in normal circumstances supplies pressure in the airflow path. Interruption of airflow may be accomplished by mechanically blocking airflow, such as by shutters, a blast gate, a damper, or other devices to close the airflow path. Interruption of the airflow through an electrostatic air cleaner may also be accomplished by ionic wind effects to counteract the airflow. Ionic wind effects to counter airflow may be achieved by incorporating a reverse-aligned electrostatic fluid accelerator. To activate the electrostatic fluid accelerator exciting electrodes may be arranged upstream from the corona electrodes and may be activated for enhanced pathogen destruction mode. Electrostatic fluid accelerators are shown in U.S. Pat. Nos. 6,504,308, 6,664,741, and 6,937,455, the disclosures of which are incorporated by reference herein. Electrostatic fluid accelerator technology may be implemented with some of the components already present for the electrostatic air cleaning features. For example, the coronal electrodes and power supply required for the electrostatic air cleaning functionality may be used for the electrostatic fluid acceleration (in this case deceleration).

It is a further object to provide supervisory control of electrostatic air cleaners in response to conditions detected by environmental, occupancy, and other sensors, for example, $CO_2$, $NO_x$, or other pathogen-detecting sensors. A significant disadvantage to smart buildings and other HVAC systems that combine air cleaning with HVAC systems is that such systems are managed to efficiently control temperature, but such management does not consider air cleaning efficiency. This is likely because temperature regulation uses far more energy than air cleaning and savings from efficiently controlling temperature exceed saving from efficiently controlling air cleaning. It is an object to manage indoor air quality regardless of the management of temperature control of a building.

It is a further object to provide systems and control methods that facilitate effective air quality control at an efficient level that is not sacrificed by temperature control. This object may be achieved by distributed electrostatic air-cleaning devices in an indoor environment. Distributed devices may be independently controlled for enhancement of energy efficiency while maintaining air quality and effect pathogen killing by elevated ozone concentration. The elevated ozone concentration may be provided to destroy pathogens collected by the electrostatic air cleaner without exposing occupants to high levels of ozone. In addition, a feature is an ability to increase indoor environmental ozone for pathogen destruction when occupants are not present.

The electrostatic device described herein may be used as an electrostatic air cleaner and/or particle separator that includes a power supply that can rapidly change the voltage across the corona electrodes and across the repelling electrodes.

It is an object to connect the electrostatic air cleaner to a Supervisory Controls module that is configured to direct changes to the voltage across the corona electrodes and across the repelling electrodes.

It is an object to connect the electrostatic air cleaner to a Supervisory Controls module that is configured to direct changes to the corona current emitted by the corona electrodes.

It is an object to connect the supervisory control module to a fan that can be integrated with the filter or can be the fan associated with the HVAC system, such that the supervisory controls module can issue commands to the fan to increase or decrease speed or reverse the directionality of the fan.

It is an object to be able to connect an ozone filter to an electrostatic air cleaner such that the filter removes ozone from the airstream prior to the airstream exiting the filter.

It is an object to increase the pathogen-killing capability of the filter by inverting the corona assembly voltage with respect to the exciting (or collecting) electrodes to produce negative corona discharge. Negative corona discharge produces about 10 greater ozone than the positive corona discharge.

It is an object to increase the pathogen-killing capability of the filter by increasing power to the corona assembly to increase ozone production. The pathogen-killing capability of the electrostatic air cleaner against pathogens that are inside the electrostatic air cleaner can be further increased by decreasing fan speed, optionally to zero, thereby increasing Ozone concentrations inside the filter. To decrease the ability of ozone to escape from the electrostatic air cleaner, the fan may be operated at a low level to produce positive airflow in the direction of the Ozone filter. Alternatively, this positive airflow may be achieved without the assistance of the fan by taking advantage of the ionic wind created by the ion-generating corona assembly.

It is an object to connect the Supervisory Control Module to data sources, including but not limited to indoor and outdoor IAQ monitors, HVAC unit control systems, outdoor air quality prediction data sources, building occupancy and activity monitors, date and time controls, and emergency alert systems.

It is an object to be able to program the Supervisory Control module to use data received from a variety of sources by implementing control algorithms that control the voltages across the corona electrodes and the repelling electrodes to achieve a variety of energy savings and filtration objectives.

It is an object to program the supervisory control module to run diagnostic routines with the results used to control the voltages across the corona and the repelling electrodes. It is a further object to receive air quality data from air quality monitors and use the air quality data to improve the performance of the system. It is a further object to receive air quality data from air quality monitors and use the air quality data to issue system status alerts.

It is an object to connect a supervisory control unit to the electrostatic air cleaner which is a component of a central HVAC system, as well as to other local air filtration units that are independent of the HVAC system to create an air filtration network that is capable of being operated by the supervisory control unit using input from a variety of data sources, and operate the electrostatic air cleaner and local air filtration units in a manner that achieves specific energy savings and air quality objectives.

The control system may be connected to adjust and/or stabilize the corona current magnitude. It is a further object to connect the electrostatic air cleaner to a Supervisory Controls module that is configured to direct changes to the corona current emitted by the corona electrodes.

An electrostatic precipitator (ESP) is a filtration device that removes aerosol particles, like dust and smoke, from a flowing gas using the force of an induced electrostatic charge minimally impeding the flow of gases through the device. Electrostatic precipitators may be used as air filters, purifiers, and/or conditioners. An electrostatic precipitator may have several types of electrodes. One type of electrode is a corona electrode. Another type may be collecting electrodes. There may be other types of electrodes such as an exciting electrode and a repelling electrode. Each type of electrode referred to herein may be a single electrode or plural electrodes. Typically, electrodes of the same type of kept at the same potential. The exciting electrode may be a single piece structure or more than one piece electrically connected. The corona electrodes may be a corona wire routed across the airflow path one time or more than one time and an electrostatic device may have one corona wire or multiple corona wires routed across an airflow path and electrically connected. The corona electrodes may be implemented in any shape. Like a needle or a razor blade as long as it creates a local high-intensity electrical field. The term "electrode set" is intended to include one or more electrodes of the same type. Electrode sets may be mounted such that one or more electrode sets may be removable to facilitate cleaning and/or replacement.

Air quality targets may vary depending on many factors. Maximum power usage is not necessarily needed to attain the required indoor air quality. The air quality output may be varied based on operating parameters.

At a lower air velocity, the voltages on both the corona electrode and the repelling electrode may be lower than at a higher air velocity. The air-cleaning efficiency of the electrostatic air cleaner may depend on the air velocity. The higher the air velocity, the lower the air cleaning efficiency. Higher cleaning efficiency may be achieved by increasing either the corona electrode voltage or the repelling electrode voltage, or both.

If outdoor air is comparatively clean, the necessary indoor air quality levels may be attained at a lower filtration efficiency.

Large particles may be easier to collect (i.e., to remove from the air stream) than smaller particles. Therefore, with lower voltages on the corona or the repelling electrodes, a greater number of large particles remain in the post-cleaner (post-particle separator) air stream than with higher voltages on the above electrodes. The voltage on the electrodes and power consumption of the electrodes may be adjusted to an optimum, not necessarily the maximum, level. Some industries like pharmaceuticals or bio-science environments where particles that may constitute pathogens or unwanted contamination are to be separated based on particle size range. This will allow separation efficiency control and control of particle size range separation in changing environments.

In an electrostatic precipitator, the corona electrode voltage, the repelling electrode voltage, and/or the collecting electrode voltage may be increased or decreased depending on the treatment amount and level of air contamination to be treated.

More specifically, the electrostatic air cleaner and particle separator may have a corona electrode for generating a stream of ions between the corona electrode and an exciting electrode facing the corona electrode. An electric power supply may apply voltages to both the corona electrodes and repelling electrodes. A collector section may include a set of collecting electrode plates and a set of repelling electrode plates. An air blower may be provided to create airflow in the device. The electrostatic air cleaner may have a particle separator function and may be capable of collecting or separating incoming particles by size, electrical conductivity, or other qualities. Another characteristic of the electrostatic air cleaner and particle separator is that it may include a power supply control component for increasing or decreasing the voltages on the above electrodes depending on the air volume of the air blower, air contamination, and resulting air purity or particle content level.

An electric power supply may impose a sufficient voltage differential between a corona electrode and an exciting (cooperating) electrode to generate a corona discharge. As a result, a stream of ions is generated. The ions may attach to particles contained in the air stream. The combined ions and particles are electrically charged. The charged components may flow with the air stream from an ionizing section toward the collection section where they may be attracted to and collected on the collecting electrodes. Collection efficiency is generally the proportion of specified particles removed from a stream. The collection (filtration) efficiency of an electrostatic precipitator depends, to a great degree, on:

1) The corona electrode voltage (and power);
2) The repelling electrode voltage;
3) Air velocity;
4) Particle sizes; and
5) Particle concentration.

Large particles may collect more ions on their surface and may obtain a greater electrical charge than smaller particles. Therefore, bigger particles may be subjected to greater electrical (Coulomb) force, which may urge the charged particles toward the collecting electrodes. The Coulomb force is generally proportional to the particle's charge.

Smaller particles may collect fewer ions and are thus under lower electrical force. Such smaller particles have a greater chance of escaping and appear in post-cleaner (post-particles separator) air.

The electrostatic air cleaner may remove particles of all size ranges, albeit, with varying removal (collecting) efficiency.

Outdoor air having a high contamination level may require air volume (air velocity) to be set to the maximum level (typically above 500 ft/min), and for the voltages on the corona electrode and the repelling electrode to be set to the maximum allowable level. The allowable level is the voltage close to the breakdown voltage of the air between electrodes. At such levels, the electrostatic air cleaner will consume maximal power and, because it is working close to the breakdown voltage level, it may produce sporadic electrical discharges like sparks or arcing.

For example, if the outdoor air is rather dirty (for example, during rush hour, or a forest fire) and contains contaminants (particles weight per volume, i.e., $p_{out}$) about 200 micrograms per cubic meter. To achieve a level, $P_{in}$, of indoor air of 2 micrograms per cubic meter the filtration efficiency Eff should be no less than $$Eff=(P_{out}-P_{in})/P_{out}=0.99 \quad (1)$$

To achieve that high filtration efficiency, the corona discharge voltage is kept near the corona breakdown voltage. As described in the T. Wen article, high filtration efficiency requires high power consumption and a large collector plate area (length).

It has been found that at a different (better) outdoor air quality level, for example, such as in light traffic conditions, inlet air may contain fewer dust particles per cubic meter. In such conditions, the filtration efficiency may be reduced to achieve the same acceptable outlet air quality. For example, relatively poorer inlet air quality may require a filtration efficiency of 99% and at a better inlet air quality, the same outlet air quality may be obtained at a 98% filtration efficiency. To achieve this level of filtration efficiency, the corona electrode voltage may be decreased somewhat, for example from a 17 KV level to a 16 kV level. Power consumption in some cases may drop up to 80% and still achieve the same indoor air quality.

Filtration efficiency may also be controlled by changing the voltage on the repelling electrode. The repelling electrode consumes much less energy than the corona electrodes and therefore the power supply for the voltage of the repelling electrode may be a lower inertia supply allowing the repelling electrode to be controlled by simpler and more cost-efficient means than would be required for an electrode requiring greater power (for example, using a linear regulator).

The airflow rate through a precipitator may be adjusted by the adjustment of a blower. Energy savings may be achieved by setting the blower to deliver less air volume. Generally, filtration efficiency decreases when the air flow rate is increased, however, the air flow rate (air velocity) may be dictated by factors other than filtration efficiency. With increased air velocity, the corona voltage on the corona and repelling electrode voltage may be required to increase to maintain efficiency. With a decreased air velocity, one or both voltages may be decreased and still maintain the same efficiency. It is an object to monitor air velocity through an electrostatic air cleaner in an HVAC system having distributed electrostatic air cleaners and adjust voltage levels on electrodes of such electrostatic air cleaner to efficiently maintain air quality.

For better air quality control with rapidly changing conditions, the voltage on the repelling electrode may follow the changing conditions quickly, while the voltage on the corona electrodes follows this change at a slower pace (i.e., changes more slowly).

Another advantage of the design is the advanced control over contamination of the corona electrode. In operation, the corona electrode may be under high voltage and therefore may be subject to electrode contamination. During operation, chemicals, like silicon, may be deposited onto the corona electrodes, which decreases the corona current and, therefore, electrostatic air cleaner's performance.

The rate of chemical deposition on the corona electrodes depends in part on the corona voltage and current. The deposition of such chemicals requires the cleaning or replacement of the corona electrodes once their performance drops. Due to this phenomenon, the corona electrode should be periodically cleaned or replaced.

Reducing the corona electrode voltage reduces deposits to the corona electrode and thus may extend the time between cleaning or replacement. At the same time the corona current may be dynamically controlled or stabilize to follow changing environmental conditions (like air humidity or air density).

An object is to have a low ozone generation at the corona discharge. This ozone generation may be reduced by the reduction of the corona voltage. This may be accomplished when the electrostatic precipitator works on lower voltage/power levels.

The release of ozone from the electrostatic precipitator can be reduced by using an ozone filter.

Ozone is also known to kill pathogens. This pathogen killing capability can be advantageously increased inside the electrostatic precipitator by increasing the Ozone concentration inside the unit by increasing the Corona electrode voltage and optionally simultaneously decreasing the air speed through the unit. This pathogen-killing capability can be implemented by an electrostatic air filter that has the ability to set this power supply to a level that maximizes ozone production, and the functionality to direct the fan to be off or at a low speed to minimize airflow. Pathogen killing can be performed during a scheduled disinfecting cycle, in the case of an HVAC filter which can be scheduled for a time when the HVAC system is not calling for heating or cooling, for example at night when building occupancy is low. This disinfecting mode can be implemented before filter change or other maintenance to reduce exposure to pathogens during filter change.

When the filter is run in this disinfecting mode, it will be advantageous to prevent Ozone from escaping from the filter. There will be a low level of airflow through the filter caused by the Corona electrodes, and at this low level of airflow, it will be possible to use a catalytic Ozone filter to prevent Ozone from escaping through the filter exit. The low level of positive ionic wind generation may prevent the Ozone from escaping through the airflow entrance.

This disinfecting mode will be particularly effective at killing pathogens trapped on the filter collector surfaces since these pathogens will be exposed continuously to the elevated Ozone levels inside the filter.

When the filter is used as an HVAC filter or an air filter for an air handling unit such as an air exchanger, if the Ozone filter is removed, the disinfecting mode will extend to disinfecting other components downstream from the filter such as the fan.

When the Ozone filter is removed, the filter will be able to produce Ozone that can be used to disinfect spaces downstream from the filter.

The Supervisory Control system is capable of receiving inputs from air quality sensors located at a variety of locations throughout the building, from external sources that monitor air quality in real-time (for example the World Air Quality Index Project https://wagi.info/) or calculate an air quality forecast (https://agicn.org/forecast/world/), from the HVAC control system that can provide data on actual and projected fan speeds and fresh air intake levels, from occupancy monitors that report real-time building occupancy levels and human activity levels that influence IAQ levels. These measures of occupancy levels and human activity levels can be used as an indicator of the need for increased filtration when IAQ sensor data is not available. Inputs from emergency notification systems that can provide data on air quality emergencies such as forest fires or biohazard incidents.

The Supervisory Control System can receive inputs from external emergency monitoring systems or other warning systems, can include a manual emergency setting, and can provide a function where these emergency warnings override other set point settings such that the filter is set it the highest filtration efficiency setting.

The Supervisory Control system, either alone or in combination with a third party IoT control system, can coordinate control of the electrostatic filters' filtration levels operating as a component of the central HVAC system, with control of other local filtration devices that are disconnected from the central HVAC system, forming a filtration network. These local devices can be operated independently, in coordination with the electrostatic filter, to provide ancillary local air filtration under a variety of situations when local air filtration would be optimal to achieve air quality or energy efficiency objectives.

The Supervisory Control system can create an air filtration network that includes the ability to control an electrostatic filter connected to the HVAC system and the ability to control local air filtration units that operate independently from the HVAC system. The Supervisory Control system can turn on and off each filtration unit independently, can increase or decrease the filtration efficiency of the electrostatic filter, can increase or decrease the fan speed of the local air filtration units, and can send a request to the HVAC control system to run the HVAC fan when there is a call for heating or cooling. The Supervisory Control system for this air filtration network receives inputs from air quality sensors located at a variety of locations throughout the building, from external sources that monitor air quality in real-time (for example the World Air Quality Index Project https://wagi.info/) or calculate an air quality forecast (https://agicn.org/forecast/world/), from the HVAC control system that can provide data on actual and projected fan speeds and fresh air intake levels, from occupancy monitors that report real-time building occupancy levels, from emergency notification systems that can provide data on air quality emergencies such as forest fires or biohazard incidents or from other programmed instructions that set air quality or energy efficiency objectives for the building that can be used by the supervisory control system to operate the networked system. The Supervisory Control System can receive inputs from internal monitoring systems, like the corona current magnitude or spark occurrence.

This air filtration network can be controlled by commands from the Supervisory Control unit to optimize overall energy use and achieve indoor air quality objectives. For example, there may be periods when the central HVAC unit is not operating since there is no call for heating or cooling. During this HVAC downtime, the Supervisory Control system can monitor indoor air quality readings from connected indoor air quality sensors, monitor occupancy levels of areas within the building, and activate local air purifiers to bring air quality measures to set point levels in occupied areas. In this situation, the Supervisory Control system could be allowed to make a call to the HVAC system to begin operation if it calculates that it is more efficient or effective to use the filtration unit connected to the HVAC system than the local units. In another example, there may be air quality issues only in one area or room in the building, and the Supervisory Control system can calculate whether it is more efficient to activate the local filter or activate the electrostatic filter connected to the HVAC system.

An electrostatic air cleaner may have an electrostatic precipitator having an air inlet, an air outlet, and at least two electrode sets. At least one air quality sensor may be positioned to monitor precipitator outlet air quality. A control system may be connected to the sensors and a power source may be connected to at least two electrode sets and responsive to the control system wherein the control system may be connected to receive the signal from the sensor and adjust a voltage at a power source output. The control system may be connected to adjust the power source outputs to achieve an air quality goal at improved energy expenditure.

The air quality sensor may be a particle size distribution sensor and/or an airflow rate sensor or some other IAQ sensor (e.g. CO2, NOx, pathogen detecting sensors, etc.) Exciting electrode(s) may be positioned to cooperate with a corona electrode set. The exciting electrode set may be grounded. One of the electrode sets may include a repelling electrode set. A collecting electrode set may be at or near ground potential. The power source may have a first output connected to a corona electrode and a second output connected to a repelling electrode. The power source output connected to the first set of electrodes is independent of the power source output connected to the second set of electrodes. The power source output may contain changeable electric potential polarity, from positive to negative. The control system may be responsive to an elevation (atmospheric pressure) sensor or an air flow rate sensor. The electrostatic precipitator may have an airflow generator connected to the power source. The airflow generator may be a fan or a blower. In a personal air cleaner, the airflow may be caused by a user breathing. The electrostatic air cleaner may be a particle separator.

Various objects, features, aspects, and advantages of the present invention will become more apparent from the following detailed description of preferred embodiments of the invention, along with the accompanying drawings in which like numerals represent like components.

Moreover, the above objects and advantages of the invention are illustrative, and not exhaustive, of those that can be achieved by the invention. Thus, these and other objects and advantages of the invention will be apparent from the description herein, both as embodied herein and as modified given any variations which will be apparent to those skilled in the art.

DETAILED DESCRIPTION OF THE PREFERRED EMBODIMENT

Before the present invention is described in further detail, it is to be understood that the invention is not limited to the embodiments described, as such may vary. It is also to be understood that the terminology used herein is to describe embodiments only, and is not intended to be limiting, since the scope of the present invention will be limited only by the appended claims.

Where a range of values is provided, it is understood that each intervening value, unless the context dictates otherwise, between the upper and lower limit of that range is encompassed within the disclosure. Where the stated range includes one or both limits, ranges excluding either or both of those included limits are also included in the disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context dictates otherwise.

All publications mentioned herein are incorporated herein by reference to disclose and describe the methods and/or materials in connection with which the publications are cited. The publications discussed herein are provided solely for their disclosure before the filing date of the present application. Nothing herein is to be construed as an admission that the present invention is not entitled to antedate such publication by prior invention. Further, the dates of publication provided may be different from the actual publication dates, which may need to be independently confirmed.

The invention is described in detail concerning preferred embodiments, and it will now be apparent from the foregoing to those skilled in the art that changes, and modifications may be made without departing from the invention in its broader aspects, and the invention, therefore, as defined in the claims, is intended to cover all such changes and modifications that fall within the true spirit of the invention.

Figure 1:
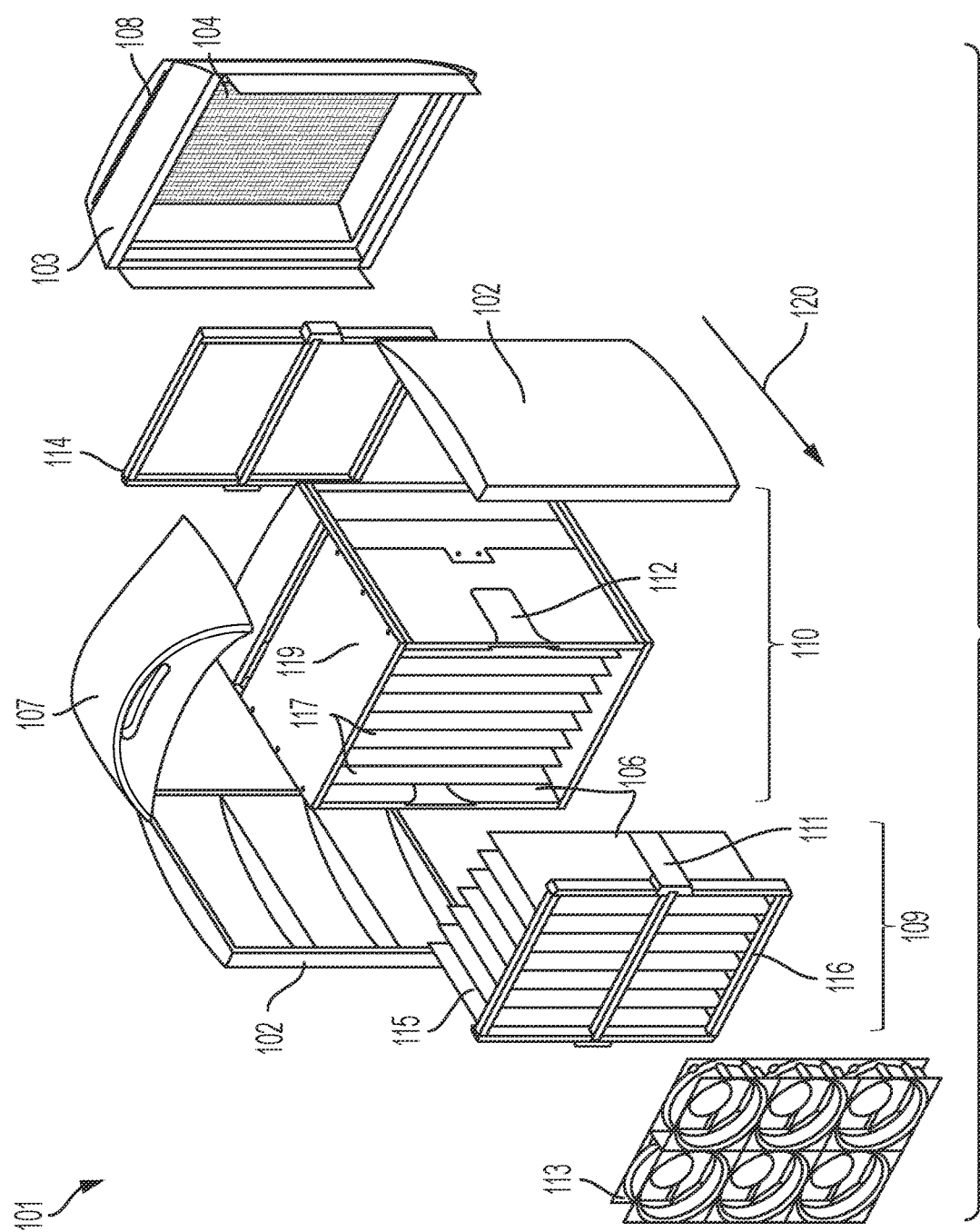
FIG. 1 shows the mechanical schematics of an embodiment of an electrostatic air cleaner.

FIG. 1 schematically shows an exploded view of an electrostatic air cleaner 101. The exploded view of FIG. 1 shows side panels 102 of a case and a top panel 107. An ionizer assembly 103 may be in the front (inlet) portion of the electrostatic air cleaner 101. A particle collection structure 106 may be in the main body of the electrostatic air cleaner 101. The ionizer assembly 103 may include emitting wires (not shown in FIG. 1, see FIG. 2). The emitting wires are referred to as corona wire(s) or corona electrode(s). A mesh-like exciting electrode 104 is shown as part of the ionizer assembly 103. The exciting electrode 104 is arranged to cooperate with the corona electrode in establishing a corona field and generating ions. One mounting arrangement for the exciting electrode may include a slot 108 to receive or extract the exciting electrode 104. The exciting electrode 104 (which is preferably earth grounded) may be easily removed through slot 108 for periodic cleaning. A topside panel 107 may include a handle. A high voltage power supply and controls may be mounted in the topside panel. The air cleaner 101 need not be configured with separate ionizer and particle collection assemblies. The components may be installed in housing without being separated into assemblies.

The particle collection structure 106 may include a particle collecting electrode assembly 109 and a particle repelling electrode assembly 110. When the particle collecting electrode assembly 109 is inserted into the particle collecting structure housing 119, rails 111 may slidably engage slots 112. The particle repelling electrode assembly 110 may be secured on the opposite side of the collecting structure housing 119 from the mounting end of the particle collecting electrode assembly 109. The particle collecting electrode assembly 109 is preferably mounted to the particle collection structure housing 119 at the end opposite the ionizer assembly 103. A fan assembly 113, may be included in the electrostatic air cleaner 101 if needed. The fan assembly may not be needed if the ionizer assembly 103 and the particle collection structure 106 of the electrostatic air cleaner 101 is in a constrained airflow path such as HVAC ductwork, in an HVAC vent, or an exhaust vent. The intended airflow direction during normal operation is shown by arrow 120.

The collecting electrode assembly 109 may include a set of parallel collecting electrode plates 115 mounted to a collecting electrode mounting structure 116. The embodiment illustrated in FIG. 1 has the collecting electrode plates 115 connected at one edge and extending from the collecting electrode mounting structure 116. The repelling electrode assembly 110 may have a similar but reversed configuration having a plurality of repelling electrode plates 117 connected to a repelling electrode mounting structure 114.

The collecting electrode assembly 109 may include a mounting rail 111.

Figure 2:
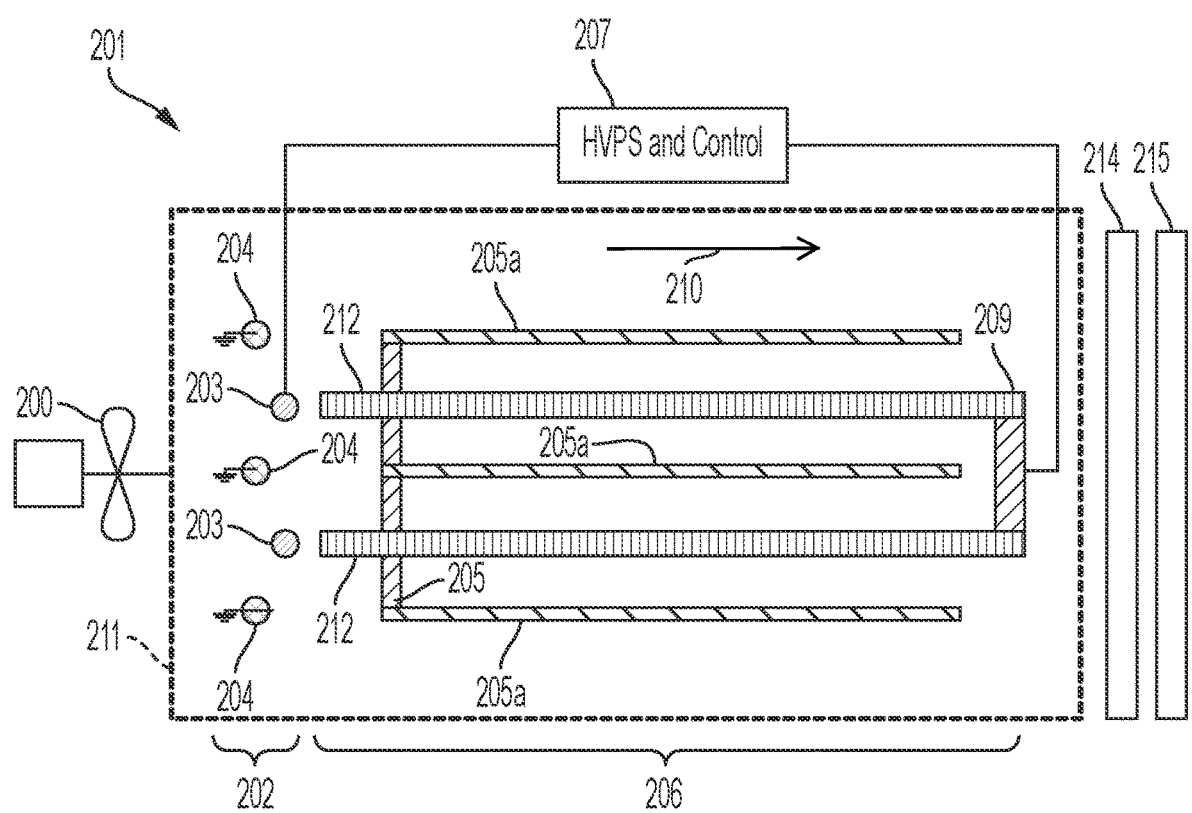
FIG. 2 shows the electrical schematics of an embodiment of an electrostatic air cleaner.

FIG. 2 schematically shows a simplified view of the electrode geometry of an electrostatic air cleaner 201. One or more fans 200 may be provided to control airflow. An ionizing stage 202 may be provided to generate ions. The intended airflow direction during normal operation is shown from left to right by arrow 210. The ionizing stage 202 may include one or more corona electrodes 203 which may be provided near an intake 211 of the electrostatic air cleaner 201. One or more exciting electrodes 204 may be provided near an intake 211 of the electrostatic air cleaner 201 and positioned to co-act with the corona electrode(s) 203. The corona electrode 203 may be a wire which is routed across the airflow path several times for example in front of each collecting electrode plate 212. The exciting electrode 204 may be a conductive grid or bars that are connected to the ground or a ground side of a high-voltage power supply in the high-voltage power system 207. The high-voltage power system 207 may also include a controller.

A particle collection stage 206 may be located downstream from the ionizing stage 202. The particle collection stage 206 may include a repelling electrode assembly 205 having one or more repelling electrode plates 205a and a collecting electrode assembly 209 having one or more collecting electrode plates 212. The collecting electrode assembly 209 is positioned to co-act with the repelling electrode assembly 205 so that charged particles move away from the repelling electrode and land on the collecting electrode plates 212. The collecting electrode plates 212 may alternate with parallel repelling electrode plates 205a in the particle collection stage 206. The ionizing stage 202 and the particle collection stage 206 are in an airflow path. The electrostatic air cleaner 201 may include one or more fans 200 to induce or affect airflow or the electrostatic air cleaner 201 may be in a constrained space with an externally induced airflow.

The airflow path may be selectively blocked by closing a blocking structure 214, such as shutters or a blast gate under the control of the high-voltage power system 207 or other controller.

The air purification device shown in U.S. Pat. No. 9,488,382 and the T. Wen article show devices with high voltages applied to both the corona electrode and the repelling electrode and show grounded exciting electrode(s) and collecting electrode(s). The devices shown in FIGS. 1 and 2 may have a high voltage applied to the corona electrodes 203, and repelling electrode assemblies 110, 205. The exciting electrode assemblies 104, 204 and collecting electrode assemblies 109, 209 may be grounded. Ionized particles are subjected to forces away from repelling electrode plates 205a and toward the collecting electrode plates 212. The particles may settle on the collecting electrode plates 212 of the collecting electrode assembly 209. All four electrode sets may have any electrical potential referenced to the ground, but the potential difference should be applied across the corona electrode 203 and exciting electrode 204 and across the repelling electrode assembly 205 and collecting electrode assembly 209. At the same time, at the maximum voltage on the corona electrode the ionizing stage would consume considerable electrical power. A high-voltage power system 207 may be connected to the electrodes. One side of the high voltage power system 207, for example, 20,000 volts, may be connected to the corona electrode 203 and another electrical potential, say, 6,000 volts to the repelling electrode assembly 205. The other side of the high voltage power system 207, for example, the ground side, may be connected to the exciting electrode 204 and the collecting electrode assembly 209.

In one mode of operation, the ionizing stage may be active to generate ions and the particle collecting stage may be in a non-active state. A non-active state may be achieved by having the collecting and repelling electrodes connected to the same voltage potential. Alternatively, the collecting and repelling electrodes may be disconnected entirely. The ions are normally driven by the electrical potential difference between the electrodes. Disconnected electrodes have no voltage difference between them and ions are not affected by their electric fields. When the collecting and repelling electrodes have the same electrical potential or are disconnected, the filtration/cleaning characteristics of the device are turned off and thus the ozone ions generated by the corona discharge will escape and increase the environmental ozone levels. This effect is enhanced by increasing the voltage applied to the corona electrode which will increase the ozone generated by the corona discharge. A further ozone generation enhancement is obtained by connecting the corona electrode to the negative potential with respect to the exciting (or collecting) electrodes. A further enhancement is obtained by deactivating any ozone filter 215 associated with the electrostatic air cleaner. The ozone filter 215 may be a series of ozone filter slats that may be opened to significantly decrease ozone filtration.

To avoid over-exposure of occupants to ozone, the electrostatic air cleaner may be connected to sensors (not shown), including one or more sensors arranged to detect inter alia building or zone occupants. The mechanisms for detecting the presence of occupants may include UV sensors, motion detectors, presence sensor, pressure sensors on the floor, or other known occupant detection systems. The system may be integrated with door locks to exclude occupants from entering ozone-filled zones. The occupant detection system may also provide for rapid venting of zones having a high concentration of ozone upon detection of an occupant.

A further object is to facilitate an increased ozone concentration in a particle collection assembly without exposing occupants to elevated ozone levels. This may be accomplished by interrupting the airflow through the electrostatic air cleaner. Interruption of airflow may be accomplished by turning off a fan 200 or other air movers that in normal circumstances supply pressure in the airflow path. Interruption of airflow may be accomplished by a mechanical block 214 to block the airflow, such as by shutters, a blast gate, a damper, or other devices to close the airflow path. The mechanical block 214 is shown at the outlet end of the airflow path. The mechanical block 214 could be located upstream from the electrode sets. In embodiments having an ozone filter 215, it is advantageous to have the mechanical block 214 between the ozone filter 215 and the ion generation assembly. Interruption of the airflow through an electrostatic air cleaner may also be accomplished by ionic wind effects to counteract the airflow. Ionic wind effects to counter airflow may be achieved by incorporating a reverse-aligned electrostatic fluid accelerator. To activate the electrostatic fluid accelerator exciting electrodes 204 may be arranged upstream from the corona electrodes 203 and may be activated for enhanced pathogen destruction mode. Electrostatic fluid accelerators are shown U.S. Pat. Nos. 6,504,308; 6,664,741; and 6,937,455, the disclosures of which are incorporated by reference herein. Electrostatic fluid accelerator technology may be implemented with some of the components already present for the electrostatic air cleaning features. For example, the corona electrodes and power supply required for the electrostatic air cleaning functionality may be used for the electrostatic fluid acceleration (in this case deceleration).

Figure 3:
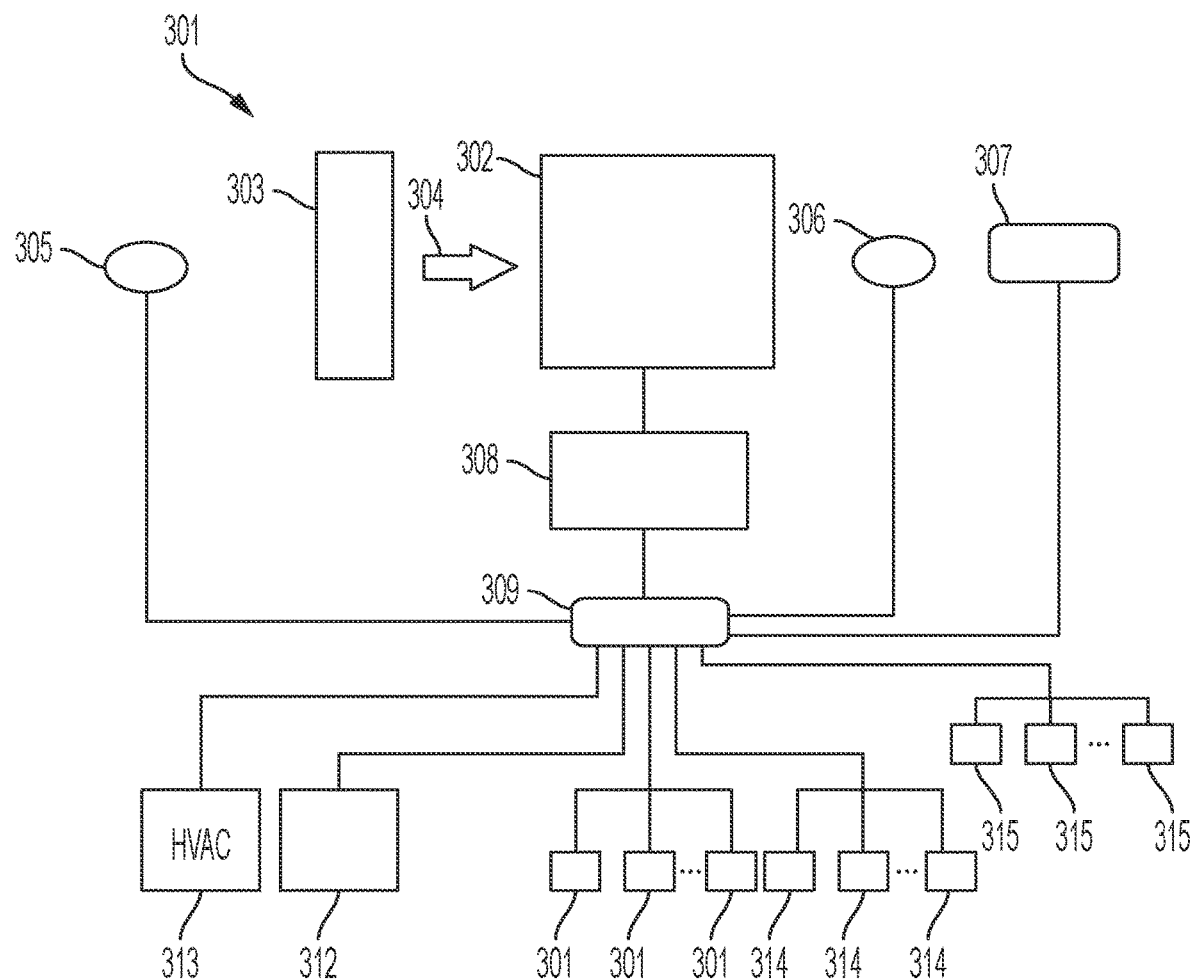
FIG. 3 shows a schematic illustration of an electrostatic air cleaner with a supervisory control system, fan, and an Ozone filter at the exit of the filter.

FIG. 3 shows a schematic diagram of an electrostatic air cleaner system that includes one or more electrostatic air cleaners 301 and associated components, for example, voltage controls responsive to air quality and other sensed conditions. The electrostatic air cleaner 301 may include a fan 303 blowing air in the direction shown by arrow 304. The electrostatic air cleaner 301 includes an electrostatic precipitator 302, which in turn has an ion-generating section 202 and particle-collecting stage 206 (schematically shown in FIG. 2) to clean incoming air. The electrostatic precipitator 302 may be powered by a power source 308 with a control system such as controller 309. The controller 309 may be separate from the high-voltage power supply and the controller may serve one or more electrostatic air cleaners. In some embodiments, the power source 308 may also power other components of the electrostatic air cleaner 301. Air quality monitors (sensors) 305 and 306 may monitor air quality and the condition of both outdoor and indoor air correspondingly. Sensor 307 may monitor the velocity of the air that passes through the electrostatic precipitator 302 or the particle-collecting stage 206. Other sensors 312 may be provided to collect information for the controller 309. Sensors 312 may include sensors for occupancy detection and other sensors.

The power source 308 may generate a high voltage that may be applied to the corona electrode 103 and the repelling electrode 105 as shown in FIG. 1.

These voltages may be controlled separately (independently) or together depending on the specific requirements.

The electrostatic air cleaning device 301 may have maximum filtration efficiency when the voltages on both the repelling and the corona electrodes are set at the maximum level.

The fan 303 speed and incoming air quality may be related to collection performance.

The air velocity of air passing through the electrostatic precipitator may be sensed by the air velocity monitor 307 may have an output connected to the controller 309. The air velocity reading may be processed by the control system (controller) 309. The control system (controller) 309 may adjust voltage levels for the power source 308 and either increase or decrease voltages across the corona 103 and repelling 105 electrodes to achieve air quality requirements, filtration efficiency, or energy savings.

An air quality sensor 305 such as an Amphenol SM-PWM-01A SMART Dust Sensor or a Waveshare Dust Sensor Detector Module with Sharp GP2Y1010AU0F may be used.

Lowering the air velocity generated by the fan 303 permits the electrostatic air cleaner 301 to maintain necessary filtration efficiency at a reduced voltage. The air velocity monitor 307 may send a corresponding signal to the control system (controller) 309. The control system (controller) 309 may decrease the voltages generated by the power source 308 in accordance with either a pre-programmed value, a measured air quality level, or a required filtration efficiency. Air quality may be measured by sensor 306, and the filtration efficiency may be calculated.

The control system may also use other environmental parameters including, but not limited to, elevation, air humidity, etc. Additional measures of environmental parameters or conditions allow for complicated and comprehensive power source 308 control via control system (controller) 309.

At high elevations, corona electrode voltage should be decreased in accordance with the Paschen law. In thinner air, the corona onset voltage and air breakdown voltage may be lower than at sea level. An additional air pressure monitor (not shown) may measure air pressure and send a corresponding signal to the control system (controller) 309.

The electrostatic air cleaner 301 may change its filtration efficiency due to other factors such as electrode contamination or other factors that cannot be readily predicted. In this case, the control system still may sense the difference in the filtration efficiency and change the power source 308 output voltages to a level where the filtration efficiency is satisfactory.

The air cleaner 301 may be installed as a recirculating air cleaner having its air inlet and air outlet in a closed space, like a building or residence, or an exterior intake system having an outdoor air inlet and an air outlet inside a closed space like a building or other enclosure. The particular air quality requirements and installation will inform the operation of the control system (controller) 309.

FIG. 3 shows a schematic diagram of an electrostatic air cleaner 301 that has a supervisory control system implemented by controller 309 that can control the power source to increase ozone production by the corona electrodes and can control the air velocity through the electrostatic precipitator 302, for example by controlling the speed of the fan 303 to decrease the rate of airflow, to increase the concentration of ozone inside the electrostatic air cleaner 301 and increase pathogen killing function inside one or more electrostatic air cleaner 301 including for pathogens that are trapped on the collecting electrodes 107.

Controller 309 may be a supervisory control capable of issuing commands to the power source 308 and other distributed electrostatic air cleaners including other networked in-duct electrostatic air cleaners 301, networked appliance type electrostatic air cleaners 314, and other components of an air quality control system 315. The other components of an air quality control system 315 may include emergency ozone venting systems, occupancy detection systems, building security systems, and outside data sources providing information useful in environmental control.

Figure 4:
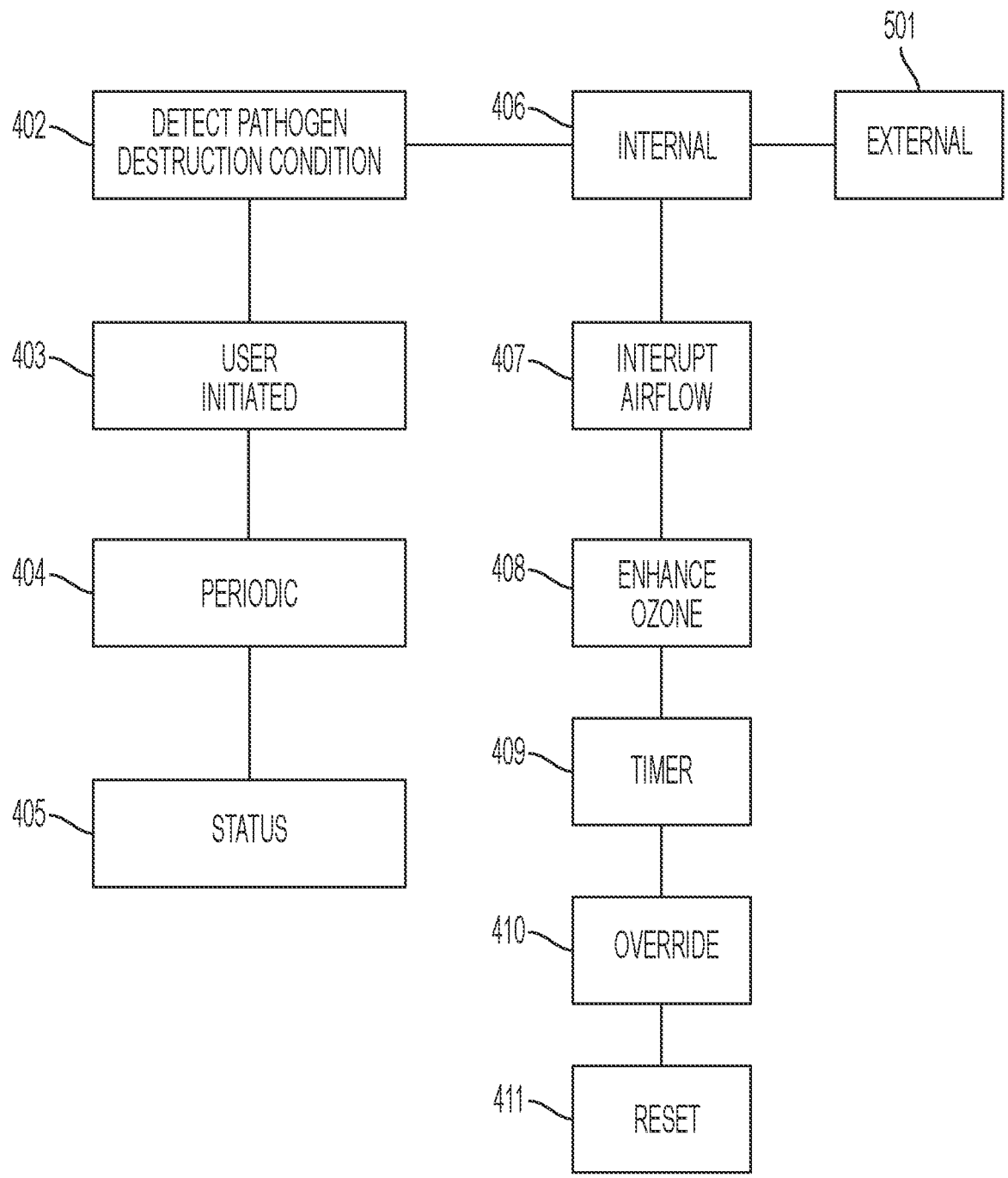
FIG. 4 shows a schematic illustration of an electrostatic air cleaner associated with an HVAC system.

FIG. 4 shows process options for an electrostatic air cleaner pathogen destruction cycle. Initially, the system will detect pathogen destruction conditions at 402. Internal pathogen destruction conditions 406 may be detected or external pathogen destruction conditions 501 may be detected. Internal conditions relate to the destruction of pathogens within the electrostatic air cleaning system. External pathogen destruction conditions 501 relate to conditions suggesting initiation of ozone enhancement outside of the electrostatic air cleaning device.

The pathogen destruction conditions 402 may include user-initiated pathogen destruction conditions 403, periodic pathogen destruction conditions 404, and device status pathogen destruction conditions 405. The user-initiated pathogen destruction conditions 403 include activation of a pathogen destruction cycle by a user.

This may be accomplished through a push-button. Alternatively, it may be accomplished through a voice command or instructions received at an interface device. The interface device may be connected to the control system of the electrostatic air cleaning device and may be hard-wired or by the wireless communication channel, for example over Wi-Fi or Bluetooth.

The external pathogen destruction process may be periodic as shown in step 404. A periodic pathogen destruction cycle 404 may be set according to a timer. For example, pathogen destruction may occur hourly, daily, weekly, or on some other time-based frequency. The pathogen destruction cycle may be initiated by device status 405. The monitoring of the conditions within a device is contemplated, although a status-based initiation considering environmental conditions such as occupancy may also be utilized.

An internal pathogen destruction cycle may be initiated at 406. Various sequences and ordering of steps may be utilized depending on device and system features, functions, and capabilities. For example, if the device includes an airflow control capability, the first step may be to interrupt airflow as shown in step 407. Airflow may be interrupted by mechanically blocking an airflow path, for example, using shutters or a blast gate. Interruption of an airflow path may also be achieved by turning a fan off or inducing a counter airflow or by electron wind generation (also referred to as electrostatic fluid accelerators). The electrostatic fluid accelerator must be oriented in the direction opposing the airflow.

The reverse airflow is particularly suitable for electrostatic air cleaners, which do not normally operate under their own airflow control. Efficient or smart HVAC systems may have central airflow control designed to enhance or optimize efficiency in temperature regulation. Temperature regulation may be a dominant factor in the management of energy expenditure; however, air quality is an ever increasingly important condition for indoor environments given the existence of potential, damaging, and/or infectious pathogens in the airflow.

The airflow interruption may be automatically controlled by activating a blast gate (also known as a cut-off), for example, of the type available from US Duct, Inc. of Kernersville NC.

Ionic wind generation having a counter direction opposite to an externally induced airflow may also be utilized. Such ionic wind generation may be controlled by adjusting voltages applied to exciting electrodes in proximity to, and upstream from corona electrodes.

The next step in the process may be to enhance ozone production at step 408. Advantageously, a baffle is used to separate any ozone filter from the corona electrodes generating elevated ozone levels. Generally, electrostatic air cleaners are tuned to balance performance against ozone generation as ozone levels must be limited in the presence of people. The control system described takes advantage of existing structures in an electrostatic air cleaner and utilizes them in a way that is contra-indicated in the art. Ozone generation may be enhanced by increasing voltage applies to the corona electrodes of an electrostatic air cleaning device.

The duration of ozone enhancement may be controlled by a timer at step 409. The ozone enhancement may be set to increase the level of pathogen destruction. In one embodiment the duration of the ozone enhancement may be related to the period between the pathogen destruction cycles. The duration of the ozone enhancement period may be set by a timer. The ozone enhancement operation may be interrupted by a mechanical override at step 410. The mechanical override may be a safety feature a switch or sensor is activated if an access panel or door to the enhanced ozone area is opened, for example, by a user attempting to service the electrostatic air cleaning device.

Electrostatic air cleaners require the replacement or servicing of the particle collecting elements. Advantageously, the pathogen destruction cycle will be activated before exposure of the particle collecting elements to destroy any live pathogens that may be harmful. The manual override may be activated if a user determines not to wait until the completion of the ozone enhancement cycle and instead opens the electrostatic air cleaner prematurely.

Step 411 is provided to reset the electrostatic air cleaner to normal operation. The reset at step 411 may include removal of the airflow interruption and discontinuing enhanced ozone production.

A device status monitor 405 may indicate that an external pathogen destruction cycle is to be initiated. In the event of indication of an external pathogen destruction cycle 501, it may be advantageous to first initiate an internal pathogen destruction cycle to avoid expelling live pathogens into the environment. The external pathogen destruction cycle 501 operates to enhance ozone concentration in an area outside of the electrostatic air cleaning device.

Figure 5:
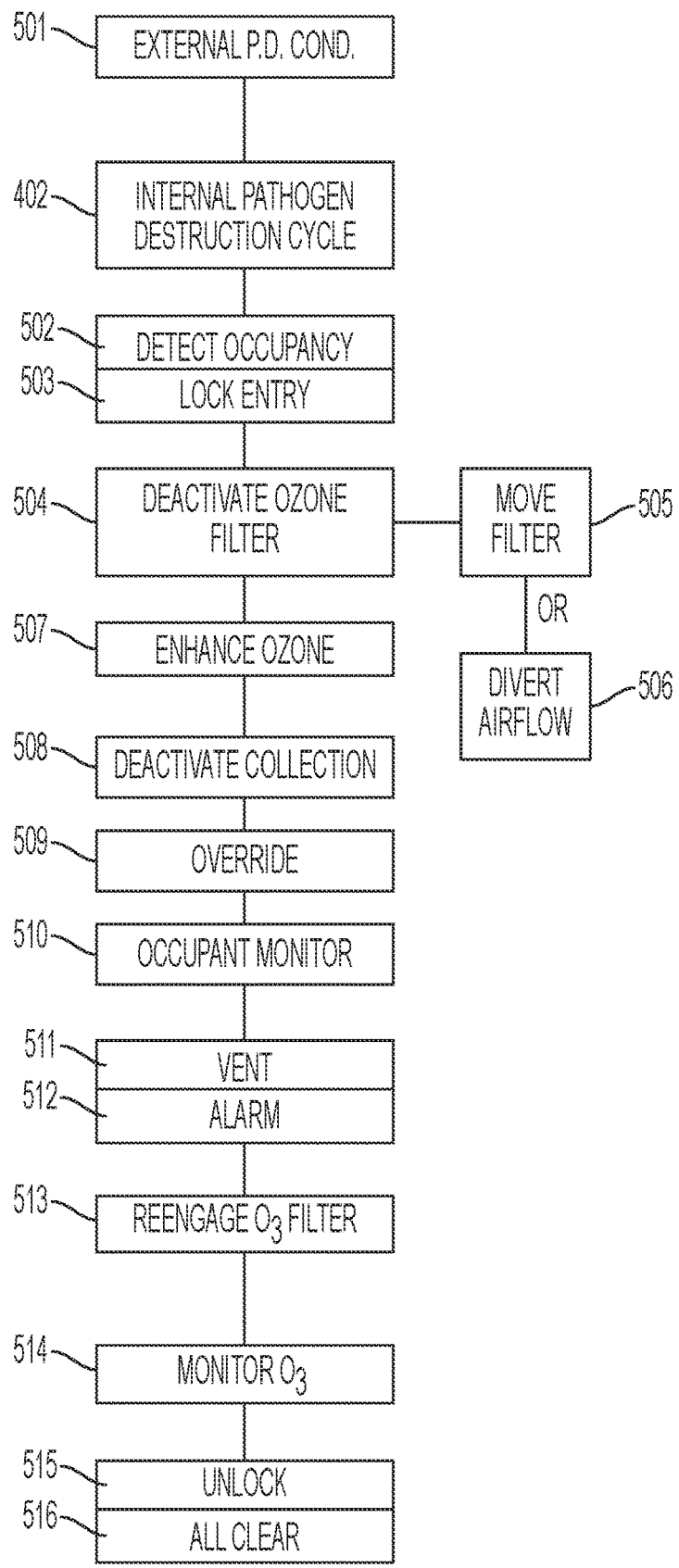
FIG. 5 shows an external pathogen destruction cycle.

FIG. 5 shows an external pathogen destruction cycle 501. The external pathogen destruction cycle 501 is initiated upon detection of external pathogen destruction conditions. As stated above the first step of an external pathogen destruction cycle may be to initiate an internal pathogen destruction cycle 402. Following the internal pathogen destruction cycle 402, there may be an occupancy detection monitor 502 as a safety to prevent increasing ozone levels outside of an electrostatic air cleaner when occupants are present. The occupancy detection may be performed by an occupancy detection subsystem, which may include various sensors such as floor weight sensors, motion detectors, heat sensors, or carbon dioxide sensors. Many smart building systems include occupancy detection sub-systems that may be suitable for detecting the presence of individuals.

The system may automatically initiate measures to block entry at 503, such as locking doors and windows to the entry of occupants. The system may also activate indicators of high ozone levels visible to occupants or approaching occupants.

Any ozone filter is deactivated at step 504. Ozone filters may be moved out of the airflow path at step 505 or the airflow may be diverted around an ozone filter at step 506.

Next, an enhanced ozone production cycle 507 may be initiated. Increasing the voltage applied to the coronal electrode may increase ozone production.

Optionally, particle collection may be deactivated at step 508. The operation of the system may have included a prior internal pathogen destruction cycle so that deactivation of particle collection at step 508 is safe even if particles are dislodged from the particle collector during deactivation and re-entrained into an airflow.

The external pathogen destruction cycle may be initiated based on a clock, based on monitoring conditions, or may be manually initiated. The system may deactivate an external pathogen destruction cycle if there is a manual override at step 509 for example. An operator may turn off the ozone enhancement. The system may also deactivate an external pathogen destruction cycle based on occupancy monitoring at step 510. Occupancy monitoring may trigger a venting process at step 511. Venting 511 may be indicated if occupancy is detected at a time when there is an unsafe level of ozone. Venting is only possible where the facility has external venting available. The occupancy monitoring 510 may also trigger an alarm at step 512 to indicate to any occupant or person approaching an enhanced ozone environment of the hazardous conditions. Also, entry may be denied.

After execution of the external pathogen destruction cycle the ozone filter may be re-activated or re-engaged and enhanced ozone generation may be terminated at step 513. Ozone levels may be monitored at step 514 and when ozone levels drop to a safe level the door locks may be released at step 515 and/or an all-clear signal may be given at step 516.

Figure 6:
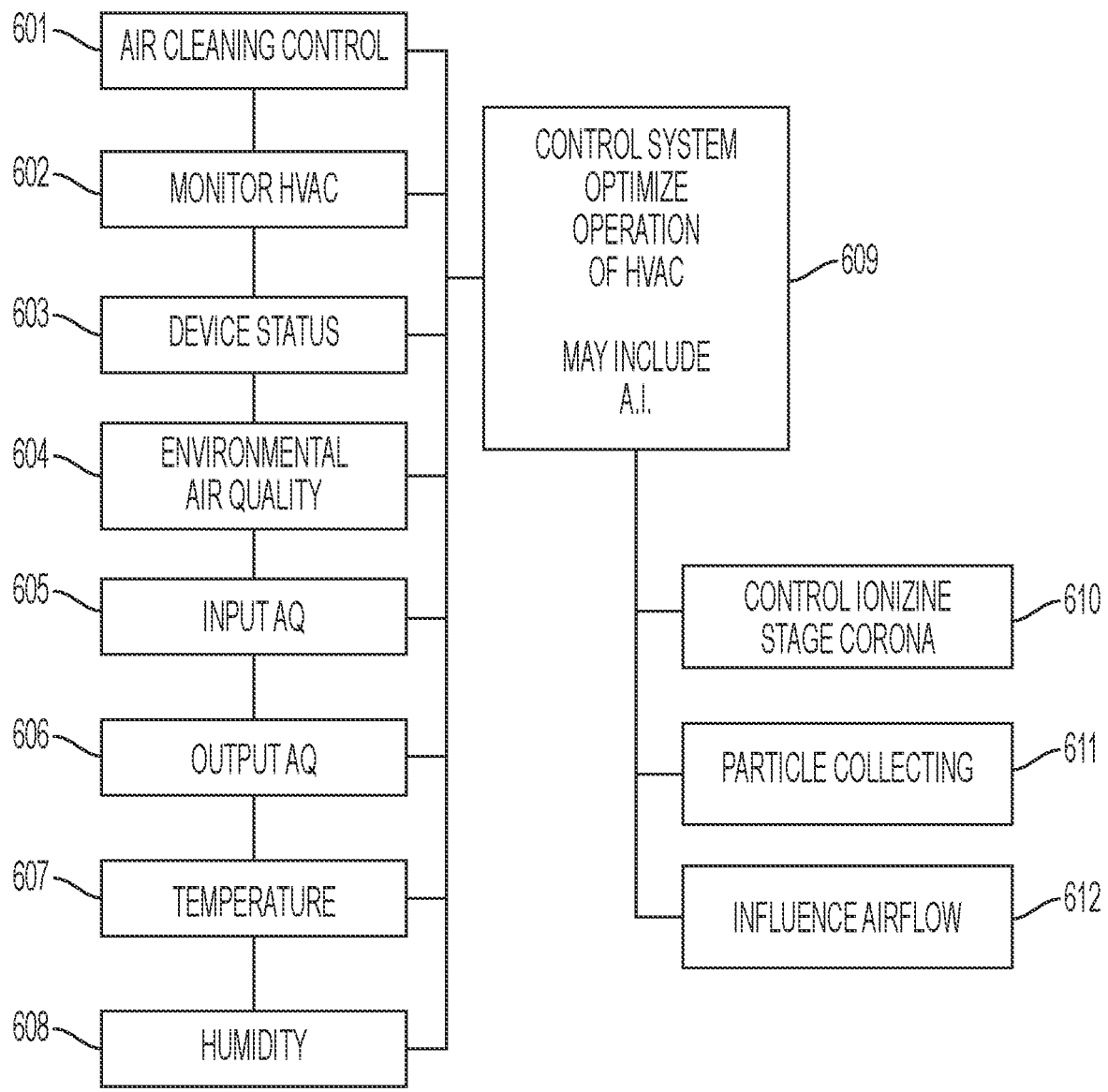
FIG. 6 shows a control process for controlling an electrostatic air-cleaning device or network of distributed air-cleaning devices.

FIG. 6 shows a control process for controlling an electrostatic air cleaning device or network of distributed air-cleaning devices. In an HVAC system where the airflow is not optimized for electrostatic air cleaning, air cleaning efficiency may be enhanced by controlling one or more electrostatic air-cleaning devices to compensate for variations in the operation of the HVAC system and variations in airflow delivery into the occupied spaces of a building. An air cleaning control routine 601 is particularly useful in smart buildings or buildings where electrostatic air cleaning is distributed and located in HVAC ventilation ducts. The system may monitor HVAC status 602 including airflow rates. Control system 601 may also monitor device status at 603, monitor environmental air quality at 604, input air quality at 605, and output air quality at 606. Other parameters may also be monitored which may affect air cleaning efficiency. Other qualities which may be monitored include air temperature at 607 and humidity at 608. The air-cleaning control process may be implemented through air cleaning control system 609 programmed to enhance the operation of the electrostatic air cleaning functionality despite not being in control of the HVAC temperature regulation operational parameters such as airflow rate. System 609 may be computer operated based on manual controls or programming. Alternatively, the control system 609 may incorporate artificial intelligence utilizing machine learning from available data and enhance control outputs from the sensor data. The system may control the electrostatic air cleaning device by controlling the operation of the ionizing stage at 610, controlling the particle collecting stage at 611, and influencing airflow at 612. Influencing airflow at 612 must be a minor contribution to the properties of airflow through an electrostatic air cleaning device, insofar as the temperature regulation controls require certain airflows, which cannot be substantially deviated from.

The techniques, processes, and apparatus described may be utilized to control the operation of any device and conserve the use of resources based on conditions detected or applicable to the device. The description herein is not intended to be limited to the utilization of all features and functions described. For example, the claims are not to be limited to a system with an ozone filter unless an ozone filter is explicitly claimed. Not all functions and features are required for all embodiments.

The invention is described in detail concerning preferred embodiments, and it will now be apparent from the foregoing to those skilled in the art that changes and modifications may be made without departing from the invention in its broader aspects, and the invention, therefore, as defined in the claims, is intended to cover all such changes and modifications that fall within the true spirit of the invention.

Thus, specific apparatus for and methods of controlling electrostatic air cleaners have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, utilized, or combined with other elements, components, or steps that are not expressly referenced.

What is claimed is:

1. An electrostatic air cleaner comprising:
    an electrostatic precipitator in an airflow path having an air inlet, an air outlet, an ozone filter, at least a corona electrode set and a second electrode set;
    a supervisory control system that issues command controls for altering voltage applied to the corona electrode set to increase ozone production; and
    means for decreasing airflow through said precipitator;
    wherein said electrostatic precipitator is a component of an HVAC system, and further comprising a means for receiving a signal from the HVAC system for when the HVAC system fan will not be circulating air, and wherein said supervisory control system that issues command controls for altering voltage applied to the corona electrode set issues command controls to increase ozone production during the time when a fan of said HVAC system is not circulating air.

2. The electrostatic air cleaner according to claim 1 wherein said command controls for altering the voltage to the corona electrode set to increase ozone production increases the voltage to the corona electrodes.

3. The electrostatic air cleaner according to claim 1 wherein said command controls for altering the voltage to the corona electrode set to increase ozone production reverses polarity of the voltage applied to the corona electrode set with respect to said second electrode set.

4. An electrostatic air filtration network comprising:
    an electrostatic precipitator in an airflow path having an air inlet, an air outlet, an ozone filter;
    at least two electrode sets;
    a high voltage power supply connected to said at least one electrode set;
    means for affecting ozone concentration; and
    a supervisory control system that issues command controls to said means for affecting ozone concentration;
    wherein said means for affecting ozone concentration increases voltage to the corona electrodes to increase ozone concentration production; and
    further comprises an occupancy sensor and wherein said means for affecting ozone concentration is operated according to said occupancy sensor reading for redirecting airflow from said ozone filter only operates when said occupancy sensor indicates people or pets are not present.

5. The electrostatic air filtration network according to claim 4 wherein said means for affecting ozone concentration reverses polarity of the high voltages power supply connection to said corona electrode(s).

6. An electrostatic air filtration network comprising:
an electrostatic precipitator having an air inlet, an air outlet, and at least two electrode sets;
at least one air quality sensor positioned to monitor air quality;
a supervisory control system connected to said air quality sensor(s);
a power source connected to at least one electrode set and responsive to said control system, wherein said control system is connected to receive one or more signal(s) from said air quality sensor(s) and adjust a voltage(s) at a power source output; and
wherein said means for affecting ozone concentration comprises an ozone filter in an airflow path and means for redirecting airflow from said ozone filter.

7. The electrostatic air filtration network according to claim 6 further comprising an occupancy sensor and said means for redirecting airflow only operates when said occupancy sensor detects a condition indicative of no people proximate to said occupancy sensor.

8. The electrostatic air filtration network according to claim 6 wherein said control system is operated according to an occupation expectation.

9. The electrostatic air filtration network comprising:
an electrostatic precipitator having an air inlet, an air outlet, and at least two electrode sets;
at least one air quality sensor positioned to monitor air quality;
a supervisory control system connected to said air quality sensor(s);
a power source connected to at least one electrode set and responsive to said control system, wherein said control system is connected to receive one or more signal(s) from said air quality sensor(s) and adjust a voltage(s) at a power source output; and
further comprising means for blocking airflow from said ozone filter.

10. The electrostatic air filtration network according to claim 9 wherein said means for blocking from said ozone filter is a shutter that is closed to decrease airflow.

11. The electrostatic air filtration network according to claim 9 wherein said means for blocking airflow from said ozone filter is a baffle arranged and activated to divert airflow away from said ozone filter.

12. The electrostatic air filtration network comprising:
an electrostatic precipitator having an air inlet, an air outlet, and at least two electrode sets;
at least one air quality sensor positioned to monitor air quality;
a supervisory control system connected to said air quality sensor(s);
a power source connected to at least one electrode set and responsive to said control system, wherein said control system is connected to receive one or more signal(s) from said air quality sensor(s) and adjust a voltage(s) at a power source output; and
wherein said control system further comprises a corona monitoring and adjustment system.

13. The electrostatic air filtration network according to claim 12 wherein said corona monitoring and adjustment system alters corona electrode operation based on status of an independently controlled HVAC air delivery to said electrostatic precipitator.

* * * * *